United States Patent [19]

Kimble et al.

[11] Patent Number: 4,528,141

[45] Date of Patent: Jul. 9, 1985

[54] PROCESS FOR PRODUCING TRITHIOCARBONIC ACID ESTERS

[75] Inventors: Kenneth B. Kimble; Clarence R. Bresson, both Bartlesville, Okla.

[73] Assignee: Phillips Petroleum Company, Bartlesville, Okla.

[21] Appl. No.: 458,505

[22] Filed: Jan. 17, 1983

[51] Int. Cl.³ .......................................... C07C 154/00
[52] U.S. Cl. ................................................. 260/455 B
[58] Field of Search ..................................... 260/455 B

[56] References Cited

U.S. PATENT DOCUMENTS

| | | | |
|---|---|---|---|
| 2,501,269 | 3/1950 | Fischer | 209/166 |
| 4,220,524 | 9/1980 | Poblete | 209/166 |
| 4,341,715 | 6/1982 | Parlman et al. | 260/455 B |

OTHER PUBLICATIONS

*J. Org. Chem.*, vol. 43, No. 14, 1978, p. 2930, by George Barany et al.
*Mining Chemicals Handbook*, No. 26, American Cyanamid Company, pp. 12 and 81.

*Primary Examiner*—Henry R. Jiles
*Assistant Examiner*—Robert C. Whittenbaugh

[57] ABSTRACT

S-Carboalkoxy-S'-alkyl trithiocarbonate, S-carboalkenoxy-S'-alkyl trithiocarbonate, S-carboalkenoxy-S'-alkenyl trithiocarbonate and S-carboalkoxy-S'-alkenyl trithiocarbonate, their use as flotation agents, and a process to make these novel compositions are disclosed.

15 Claims, No Drawings

PROCESS FOR PRODUCING TRITHIOCARBONIC ACID ESTERS

This invention relates generally to novel chemical compositions. In one aspect, the invention relates to a process for making such compositions. In another aspect, the invention relates to ore flotation processes employing such novel compositions.

Froth flotation is a process for recovering and concentrating minerals from ores. In a froth flotation process, the ore is crushed and wet ground to obtain a pulp. Additives such as mineral flotation or collecting agents, frothing agents, suppressants, stabilizers, etc. are added to the pulp to assist separating valuable minerals from the undesired or gangue portions of the ore in subsequent flotation steps. The pulp is then aerated to produce a froth at the surface. The minerals which adhere to the bubbles or froth are skimmed or otherwise removed and separated. The froth product or the reject product or both can then be further processed to obtain the desired minerals. Typical mineral flotation collectors include xanthates, amines, alkyl sulfates, arenes, sulfonates, dithiocarbamates, dithiophosphates, and thiols.

It is known from the art that some organic derivatives of trithiocarbonic acid are useful as flotation agents. U.S. Pat. No. 1,659,396, for instance, describes diethyl trithiocarbonate and the production thereof. U.S. Pat. No. 3,166,580 describes dicyclopentyl trithiocarbonates and their production as well as the utility of these compounds as flotation agents.

It is a continuing goal in the ore-processing industry to increase the productivity of ore flotation processes and, above all, to provide specific procedures which are selective to one ore or metal over other ores or metals present in the treated material.

It is an object of this invention to provide new trithiocarbonates.

A further object of this invention is to provide a process for making such trithiocarbonates.

Yet another object of this invention is to provide an ore flotation process wherein such new trithiocarbonates are used as flotation agents.

These and other objects, advantages, details, features and embodiments of this invention will become apparent to those skilled in the art from the following detailed description of the invention and the appended claims.

In accordance with this invention it has now been found that S-carboalkoxy-S'-alkyl trithiocarbonates, S-carboalkenoxy-S'-alkyl trithiocarbonates, S-carboalkenoxy-S'-alkenyl trithiocarbonates and S-carboalkoxy-S'-alkenyl trithiocarbonates are very effective and selective ore flotation agents.

Thus, in accordance with a first embodiment of this invention, novel compositions of matter are provided which can be characterized by the formula

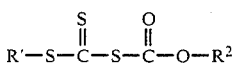

wherein R' is selected from the group consisting of lower alkyl and lower alkenyl radicals, and wherein $R^2$ is selected from the group consisting of lower alkyl and lower alkenyl radicals.

In accordance with a second embodiment of the invention there is provided a process for producing the above-defined novel trithiocarbonates. This process comprises;

(a) reacting an alkali metal or ammonium hydroxide having the formula;

wherein M is selected from the group consisting of Li, Na, K and $NH_4^+$, with a mercaptan having the formula

wherein R' is selected from the group consisting of lower alkyl and lower alkenyl radicals to form

(b) reacting R'—S—M and $CS_2$ to form

(c) reacting the product of formula (IV) with a haloformic ester having the formula

wherein X is selected from the group consisting of Cl, Br and I, and $R^2$ is selected from the group consisting of lower alkyl and lower alkenyl radicals, to form a trithiocarbonate having the formula

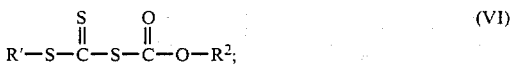

and (d) recovering the product of formula (VI) as the product of the process.

The detailed operating conditions for the individual steps are not critical and specific values for the steps can be seen from the following examples. Generally the first step of the reaction, namely the reaction of the mercaptan and the alkali metal hydroxide or ammonium hydroxide, is carried out in an aqueous environment and at a temperature in the range from about 25° C. to about 100° C. and under a pressure of from about 0 to about 500 psig. The reaction time for this first step is somewhat dependent upon the other reaction conditions but will generally be in the range of from about 1 to about 2 hours.

The second step conditions of this process, namely the reaction of the compound of formula (III) with carbon disulfide, are generally in the same ranges as those for the first step.

The reaction of the product of formula (IV) with the haloformic ester will generally be carried out by a slow addition of the two compounds and mixing. The exothermic reaction is generally carried out at a temperature in the range from about 25° C. to about 100° C. and at a pressure in the range from about 0 to about 500 psig for a time in the range from about 1 to about 10 hours.

The separation of the product of formula (VI) is carried out by standard techniques.

A further embodiment of this invention resides in an ore flotation process. More specifically, such further embodiment of this invention resides in a process for separating valuable ore materials from gangue materials. The ore flotation process of this invention distinguishes over the known ore flotation processes primarily in the employment of a new flotation agent to be defined. Otherwise the recovery process involves crushing of the ore and ore grinding to obtain a pulp. In this pulp the flotation agent is incorporated and the pulp is aerated to produce a froth at the surface which is rich in valuable ore materials but depleted of the gangue materials or vice versa. The ore materials, optionally, after additional flotation and frothing steps, are recovered. Frothing agents, selective suppressants and stabilizers which are well known in the art can be used in the various steps.

The trithiocarbonates useful in the ore flotation process of this invention are characterized by the formula

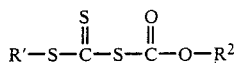

wherein R' is selected from the group consisting of alkyl and alkenyl radicals having from 1 to 12 carbon atoms, and $R^2$ is selected from the group consisting of alkyl and alkenyl radicals having from 1 to 12 carbon atoms. Examples of such compounds useful as flotation agents in the process of this invention are those generally characterized as S-carboalkoxy-S'-alkyl trithiocarbonate, S-carboalkenoxy-S'-alkyl trithiocarbonate, S-carboalkenoxy-S'-alkenyl trithiocarbonte and S-carboalkoxy-S'-alkenyl trithiocarbonate, such as for example
S-carbomethoxy-S'-methyl trithiocarbonate,
S-carbethoxy-S'-ethyl trithiocarbonate,
S-carbobutoxy-S'-butyl trithiocarbonate,
S-carbethoxy-S'-octyl trithiocarbonate,
S-carbethoxy-S'-decyl trithiocarbonate,
S-carbethoxy-S'-dodecyl trithiocarbonate,
S-carbethoxy-S'-allyl trithiocarbonate,
S-carballyloxy-S'-ethyl trithiocarbonate,
and the like, and mixtures of any two or more thereof.

Hereinafter the designation S and S' in the nomenclature is omitted for convenience, but it will be understood that the trithiocarbonates herein disclosed are those having the S- and S'-substitution.

The presently preferred composition used as the flotation agent in the process of this invention is carbethoxy ethyl trithiocarbonate.

The amount of carboalkoxy alkyl trithiocarbonate or carboalkoxy alkenyl trithiocarbonate employed in the process of this invention is not critical. The quantity will depend upon other process parameters. Generally, the amount of carboalkoxy alkyl trithiocarbonate or carboalkoxy alkenyl trithiocarbonate employed in the process will be in the range of from about 0.001 lb to about 1.0 lb of the carboalkoxy alkyl trithiocarbonate and/or carboalkoxy alkenyl trithiocarbonate per ton of ore. Preferably the ore flotation collector will be used in a quantity in the range from about 0.01 to about 0.3 lb/ton of ore.

It is generally believed that the trithiocarbonates disclosed herein are useful for separating any valuable metal sulfide from its corresponding gangue material. It is also understood that the trithiocarbonates may separate a mixture of metals that are contained in a particular mining deposit or ore, said mixture being further separated by subsequent froth flotations or any other conventional separating methods. The trithiocarbonates herein disclosed are particularly useful for separating molybdenum and copper minerals from the total ore. Examples of such molybdenum-bearing ores include, but are not limited to such materials as

| Molybdenum-Bearing ores: | |
|---|---|
| Molybdenite | $MoS_2$ |
| Wulfenite | $PbMoO_4$ |
| Powellite | $Ca(Mo,W)O_4$ |
| Ferrimolybdite | $Fe_2Mo_3O_{12}.8H_2O$ |

Other metal bearing ores within the scope of this invention are, for example, but not limited to, such materials as

| Copper-bearing ores: | |
|---|---|
| Covellite | CuS |
| Chalcocite | $Cu_2S$ |
| Chalcopyrite | $CuFeS_2$ |
| Bornite | $Cu_5FeS_4$ |
| Cubanite | $Cu_2SFe_4S_5$ |
| Valerite | $Cu_2Fe_4S_7$ or $Cu_3Fe_4S_7$ |
| Enargite | $Cu_3(As,Sb)S_4$ |
| Tetrahedrite | $Cu_{12}Sb_4S_{13}$ |
| Tennanite | $Cu_{12}As_4S_{13}$ |
| Cuprite | $Cu_2O$ |
| Tenorite | CuO |
| Malachite | $Cu_2(OH)_2CO_3$ |
| Azurite | $Cu_3(OH)_2CO_3$ |
| Antlerite | $Cu_3SO_4(OH)_4$ |
| Brochantite | $Cu_4(OH)_6SO_4$ |
| Atacamite | $Cu_2Cl(OH)_3$ |
| Chrysocolla | $CuSiO_3$ |
| Famatinite | $Cu_3(Sb,As)S_4$ |
| Bournonite | $PbCuSbS_3$ |
| Lead-Bearing ore: | |
| Galena | PbS |
| Antimony-Bearing ore: | |
| Stibnite | $Sb_2S_3$ |
| Zinc-Bearing ores: | |
| Sphalerite | ZnS |
| Zincite | ZnO |
| Smithsonite | $ZnCO_3$ |
| Silver-Bearing ores: | |
| Argentite | $Ag_2S$ |
| Stephanite | $Ag_5SbS_4$ |
| Hessite | $Ag_2Te$ |
| Chromium-Bearing ores: | |
| Daubreelite | $FeSCrS_3$ |
| Chromite | $FeO.Cr_2O_3$ |
| Iron-Bearing ores: | |
| Pyrite | $FeS_2$ |
| Marcasite | $FeS_2$ |
| Pyrrhotite | $Fe_7S_8$ |
| Nickel-Bearing ores: | |
| Pentlandite | (FeNi)S |
| Millerite | NiS |
| Niccolite | NiAs |
| Gold-Bearing ores: | |
| Sylvanite | $(AuAg)Te_2$ |
| Calaverite | $AuTe_2$ |
| Platinum-Bearing ores: | |
| Cooperite | $Pt(AsS)_2$ |
| Sperrylite | $PtAs_2$ |
| Uranium-Bearing ores: | |
| Pitchblende | $U_2O_5(U_3O_8)$ |
| Gummite | $UO_3.nH_2O$. |

The presently preferred ores in connection with which the process of this invention is applied are molybdenum, copper and iron ores or minerals.

Separation Conditions

Any froth flotation apparatus can be used in this invention. The most commonly used commercial flotation machines are the Agitar (Galigher Co.), Denver Sub-A (Denver Equipment Co.), and the Fagergren (Western Machinery Co.). Smaller laboratory scale apparatus such as the Hallimond cell can also be used.

The instant invention was demonstrated in tests conducted at ambient room temperature to about 37° C. (100° F.) and atmospheric pressure. However, any temperature or pressure generally employed by those skilled in the art is within the scope of this invention.

The following examples serve to illustrate this invention without undue limitation of the scope thereof.

EXAMPLE I

This example describes the preparation of an alkyl formate ester of trithiocarbonic acid, namely, S-carbethoxy-S'-ethyl trithiocarbonate. 1000 milliliters of water and 21 grams (0.53 mole) of sodium hydroxide were added to a 3-necked glass flask fitted with a stirrer, dropping funnel, thermometer and condenser. After the hydroxide had dissolved, 31.1 grams (0.5 mole) of ethyl mercaptan was slowly added to the flask. When the reaction temperature had cooled below 45° C., 38.1 grams (0.5 mole) of carbon disulfide was slowly added to the flask with stirring. After all of the carbon disulfide had been added, the mixture was stirred for about 1 hour during which time the temperature decreased to about 25° C. Ethyl chloroformate, 54.3 grams (0.5 mole), was slowly added dropwise to the flask during which time the temperature rose to about 55° C. and a second bright red phase separated. When all the ethyl chloroformate was in solution, the mixture was stirred for 2 more hours. The red (top) organic phase was separated from the nearly colorless aqueous phase. There was obtained 91.5 grams of the red organic layer which was assumed to be essentially all S-carbethoxy-S'-ethyl trithiocarbonate. Analysis by GLC was unsuccessful because 3 main peaks (about 20% each) eluted as well as several smaller peaks. This was interpreted as being decomposition. The process was repeated as described above with the exception that 45.1 grams (0.5 mole) of n-butyl mercaptan was used instead of the ethyl mercaptan. The crude product, 109.2 grams, thus produced was assumed to be S-carbethoxy-S'-n-butyl trithiocarbonate.

EXAMPLE II

This example describes the procedure whereby the S-carbethoxy-S'-ethyl trithiocarbonate prepared in Example I was evaluated as an ore flotation reagent. The example also includes a comparison with other commerical ore flotation mineral collectors using the same ore. To a ball mill was added 750 grams of a Cu-Ni bearing ore plus 1125 milliliters of water and the mixture ground for 16 minutes 48 seconds. The thus produced slurry or pulp was transferred to a 2.5 liter capacity Denver D-12 flotation cell along with enough water to raise the surface of the slurry to within 1 inch of the lip. When necessary, the pH was adjusted to 5 with concentrated $H_2SO_4$. There was added in Runs 5 and 6 with stirring (about 1500 rpm) 0.1 lb/ton pine oil and 0.2 lb/ton S-carbethoxy-S'-ethyl trithiocarbonate prepared in Example I. After conditioning for 3 minutes, the slurry was floated for 5 minutes. The concentrate was filtered, dried and analyzed. The procedure was repeated but the inventive collector was replaced with commercial collectors (Runs 1-4). In Runs 1 and 2 (made in duplicate) the collector was 0.2 lb/ton of sodium ethyl xanthate (from American Hoechst) used as a 1% aqueous solution. In Runs 3 and 4 (made in duplicate) the collector was ORFOM CO800 (40% aqueous sodium n-butyl trithiocarbonate from Phillips Petroleum Company). The results of these runs are listed in Table I where it can be seen that the inventive collector S-carbethoxy-S'-ethyl trithiocarbonate (Runs 5 and 6) contributes to higher recovery percentages of Cu and Ni than do the other two commercial collectors (Runs 1 through 4).

TABLE I

Comparison of Cu—Ni Collectors
(750 grams ore)

| Run | Collector 0.2 lb/ton | Concentrate, grams Total wt | Cu | Ni | % Recoveries Cu | Ni |
|---|---|---|---|---|---|---|
| Controls | | | | | | |
| 1 | Na Ethyl Xanthate[a] | 51.87 | 6.27 | 2.59 | 73.68 | 32.73 |
| 2 | Na Ethyl Xanthate | 57.03 | 6.78 | 2.68 | 76.27 | 32.84 |
| | | | | Average = | 74.98 | 32.79 |
| 3 | Na Butyl Trithiocarbonate[b] | 59.00 | 7.08 | 2.77 | 80.43 | 34.41 |
| 4 | Na Butyl Trithiocarbonate[b] | 67.05 | 6.91 | 3.21 | 80.54 | 39.17 |
| | | | | Average = | 80.49 | 36.79 |
| Invention | | | | | | |
| 5 | S—Carbethoxy-S'—Ethyl Trithiocarbonate | 81.87 | 7.08 | 4.83 | 82.23 | 55.84 |
| 6 | S—Carbethoxy-S'—Ethyl Trithiocarbonate | 92.16 | 7.43 | 5.07 | 84.24 | 59.99 |
| | | | | Average = | 83.29 | 57.92 |

[a] From American Hoechst, used as a 1% aqueous solution.
[b] ORFOM CO800 from Phillips Petroleum Company, supplied as a 40% solution.

EXAMPLE III

This example gives a comparison between two collectors that are similar in chemical structure, namely, the inventive collector S-carbethoxy-S'-ethyl trithiocarbonate, and a commercial collector, S-carbethoxy-O-ethyl xanthate (Minerec A).

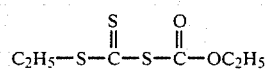

S—carbethoxy—S'—ethyl trithiocarbonate

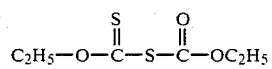

S—carbethoxy—O—ethyl xanthate

The procedure described in Example II was repeated at a pH of about 8.6 using the collectors disclosed. The results listed in Table II show a significant improvement in Cu and Ni recovery using the inventive trithiocarbonate (Runs 9 and 10) compared to the commercial xanthate (Runs 7 and 8).

TABLE II

Effects of Chemical Structure on the Efficiency of Mineral Collectors (750 grams ore)

| Run | Collector 0.2 lb/ton | Concentrate, grams Total wt | Cu | Ni | % Recoveries Cu | Ni |
|---|---|---|---|---|---|---|
| Controls | | | | | | |
| 7 | S—Carbethoxy-O—Ethyl Xanthate[a] | 50.7 | 5.66 | 1.93 | 66.72 | 29.75 |
| 8 | S—Carbethoxy-O—Ethyl Xanthate[a] | 55.2 | 6.28 | 2.43 | 72.32 | 37.47 |
| | | | | Average = | 69.52 | 33.61 |
| Invention | | | | | | |
| 9 | S—Carbethoxy-S'—Ethyl Trithiocarbonate | 59.8 | 6.92 | 2.57 | 76.57 | 40.19 |
| 10 | S—Carbethoxy-S'—Ethyl Trithiocarbonate | 61.5 | 6.56 | 2.52 | 76.86 | 38.55 |
| | | | | Average = | 76.72 | 39.37 |

[a]Minerec A (from Minerec Chem. Co.)

In summary, the data herein disclosed reveal that the novel compound S-carbethoxy-S'-ethyl trithiocarbonate is useful as a ore flotation agent. The compound is particularly suited for floating Cu and Ni sulfides.

Reasonable variations and modifications which will become apparent to those skilled in the art can be made in this invention without departing from the spirit and scope thereof.

We claim:

1. The composition represented by the formula $$R'-S-\overset{\overset{S}{\|}}{C}-S-\overset{\overset{O}{\|}}{C}-O-R^2$$

wherein R' is selected from the group consisting of lower alkyl and lower alkenyl radicals, and wherein $R^2$ is selected from the group consisting of lower alkyl and lower alkenyl radicals.

2. A composition in accordance with claim 1 wherein R' is selected from the group consisting of alkyl and alkenyl radicals having from 1 to 12 carbon atoms.

3. A composition in accordance with claim 2 wherein $R^2$ is selected from the group consisting of alkyl and alkenyl radicals having from 1 to 12 carbon atoms.

4. A composition in accordance with claim 1 wherein $R^2$ is selected from the group consisting of alkyl and alkenyl radicals having from 1 to 12 carbon atoms.

5. S-carboalkoxy-S'-alkyl trithiocarbonate.
6. S-carboalkoxy-S'-alkenyl trithiocarbonate.
7. S-carboalkenoxy-S'-alkyl trithiocarbonate.
8. S-carboalkenoxy-S'-alkenyl trithiocarbonate.

9. A process for producing a trithiocarbonate having the formula $$R'-S-\overset{\overset{S}{\|}}{C}-S-\overset{\overset{O}{\|}}{C}-O-R^2 \quad (I)$$

wherein R' is selected from the group consisting of lower alkyl and lower alkenyl radicals, and wherein $R^2$ is selected from the group consisting of lower alkyl and lower alkenyl radicals, comprising the steps of:

(a) reacting a hydroxide having the formula $$M-OH \quad (II),$$

wherein M is selected from the group consisting of Li, Na, K and $NH_4^+$, with a mercaptan having the formula $$R'-S-H \quad (III).$$

wherein R' is selected from the group consisting of lower alkyl and lower alkenyl radicals to form $$R'-S-M \quad (IV);$$

(b) reacting R'—S—M and $CS_2$ to form $$R'-S-\overset{\overset{S}{\|}}{C}-S-M; \quad (V)$$

(c) reacting the product of formula (V) with a haloformic ester having the formula $$X-\overset{\overset{O}{\|}}{C}-O-R^2, \quad (VI)$$

wherein X is selected from the group consisting of Cl, Br and I, and $R^2$ is selected from the group consisting of lower alkyl and lower alkenyl radicals, to form a trithiocarbonate having the formula (I) and;

(d) recovering said trithiocarbonate as the product of the process.

10. A process in accordance with claim 9 wherein X is Cl.

11. A process in accordance with claim 9 wherein said hydroxide is sodium hydroxide.

12. A process in accordance with claim 9 wherein $R^2$ is an ethyl radical.

13. A process in accordance with claim 12 wherein X is Cl.

14. A process in accordance with claim 12 wherein R' is an ethyl radical.

15. The composition produced by the process of claim 9.

* * * * *